United States Patent [19]
Hargreaves

[11] Patent Number: 5,981,526
[45] Date of Patent: Nov. 9, 1999

[54] USE OF TACHYKININ ANTAGONIST AND RIZATRIPTAN

[75] Inventor: Richard John Hargreaves, London, United Kingdom

[73] Assignee: Merck Sharp & Dohme Ltd., Hoddesdon, United Kingdom

[21] Appl. No.: 08/943,398

[22] Filed: Oct. 3, 1997

[30] Foreign Application Priority Data

Oct. 7, 1996 [GB] United Kingdom .................. 9620777

[51] Int. Cl.⁶ .................................................. A61K 31/535

[52] U.S. Cl. ..................................... 514/236.2; 514/231.5; 514/235.8; 514/236.5; 514/237.2; 514/383

[58] Field of Search .................................. 514/231.5, 383, 514/235.8, 236.2, 236.5, 237.2

[56] References Cited

U.S. PATENT DOCUMENTS

| 5,451,588 | 9/1995 | Baker et al. | 514/323 |
| 5,719,147 | 2/1998 | Dorn et al. | 514/227.5 |
| 5,744,482 | 4/1998 | Cohen et al. | 514/316 |

FOREIGN PATENT DOCUMENTS 0 497512  1/1992  European Pat. Off. .

*Primary Examiner*—Frederick Krass
*Attorney, Agent, or Firm*—J. Eric Thies; David L. Rose

[57] ABSTRACT

The present invention relates to a method for the treatment or prevention of migraine, which method comprises administration to a patient in need of such treatment an amount of a tachykinin antagonist and an amount of rizatriptan such that together they give effective relief. There is also provided pharmaceutical compositions and products comprising a tachykinin antagonist and rizatriptan.

2 Claims, No Drawings

USE OF TACHYKININ ANTAGONIST AND RIZATRIPTAN

CROSS REFERENCE TO RELATED APPLICATIONS

This application claims priority under 35 U.S.C. § 119(a) from Great Britain Application No. 9620777.4, filed Oct. 17, 1998.

This invention relates to the treatment or prevention of migraine by the administration of a combination of a tachykinin antagonist, in particular an NK-1 receptor antagonist, and the 5-HT$_{1D}$ agonist rizatriptan.

Migraine is a recurrent, often familial symptom complex of periodic attacks of vascular headache, which is often associated with nausea and vomiting. Attacks are preceded by constriction of the cranial arteries and commence with vasodilatation. (Dorland's Illustrated Medical Dictionary) 27th edition, WEB. Saunders Co., 1988). Migraine affects approximately 17% of adult women and 6% of adult men. Stewart W. F., Shechter A, Rasmussen, B. K. "Migraine prevalence: a review of population-based studies", Neurology, 1994, 44(suppl. 4) S17–S23.

Treatment regimens include the use of OTC analgesics, prescription analgesics, ergotamine and derivatives, and administration of parenterally, orally and intranasally active 5-HT$_{1B/1D}$ receptor agonists.

5-HT$_{1B/1D}$ receptor agonist anti-migraine agents are believed to exert their effects through selective actions at peripheral and central 5-HT$_{1B}$ and 5-HT$_{1D}$ receptors. First, activation of 5-HT$_1$ receptors, probably 5-HT$_{1B}$ receptors, on cranial vasculature selectively constricts the blood vessels that are dilated during a migraine attack. Second, 5-HT$_{1B/BD}$ receptor agonists inhibit the trigeminal sensory pathways that convey pain producing stimuli from the cranium into the central nervous system (CNS). Activation of trigeminal sensory nerves triggers the release of substances (e.g. substance P, neurokinin A and calcitonin gene related peptide) that produce vasodilation and inflammation around blood vessels in sensitive tissues such as the dura mater and that relay the pain message to neurones in the CNS. Agonists acting at the 5-HT$_1$ receptors, probably 5-HT$_{1B}$ receptors, that are present in the trigeminal nerves prevent the release of these substances leading to decreased dilation of sensitive blood vessels, decreased inflammation and reduced central pain transmission. In addition to the trigeminal nerves, there are other parasympathetic perivascular nerve fibres that contain vasodilator substances (e.g. acetyl choline, vasointestinal polypeptide) in the cranial vasculature and these may also become activated in migraine thereby increasing cranial vessel diameter and provoking activation of sensory nerves.

The neuronal cell bodies that give rise to the trigeminal sensory nerve fibres reside in the trigeminal ganglia and those parasympathetic fibres more superficially in the sphenopalatine ganglia (SPG) and otic ganglia.

The onset of action time for oral and intranasal 5-HT$_{1B/1D}$ receptor agonists ranges from about 30 minutes to about 2 hours depending upon the choice of 5-HT$_{1B/1D}$ receptor agonist and the route of administration. Recurrence of migraine is approximately 30–40% within 24 hours after administration of drug.

What is needed is a formulation and method of treatment that provides for rapid onset of action to combat migraine when it is first realized, as well as a method of treatment and formulation which provides for sustained action that prevents reccurrence.

Rizatriptan is a 5-HT$_{1B/1D}$ receptor agonist of the structure

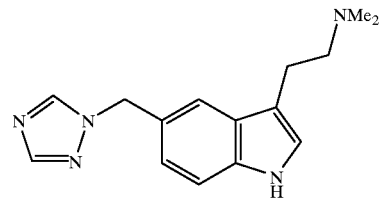

which is also known as N,N-dimethyl-2-[5-(1,2,4-triazol-1-yl-methyl)-1H-indol-3-yl]ethylamine (MK-462).

The present invention accordingly provides the use of a tachykinin antagonist and rizatriptan for the manufacture of a medicament for the treatment or prevention of migraine.

The present invention also provides a method for the treatment or prevention of migraine, which method comprises administration to a patient in need of such treatment an amount of a tachykinin antagonist and an amount of rizatriptan such that together they give effective relief.

In a further aspect of the present invention, there is provided a pharmaceutical composition comprising a tachykinin antagonist and rizatriptan, together with at least one pharmaceutically acceptable carrier or excipient.

It will be appreciated that the tachykinin antagonist and rizatriptan may be present as a combined preparation for simultaneous, separate or sequential use for the treatment or prevention of migraine. Such combined preparations may be, for example, in the form of a twin pack.

In a further or alternative aspect of the present invention, there is therefore provided a product comprising a tachykinin antagonist and rizatriptan as a combined preparation for simultaneous, separate or sequential use in the treatment or prevention of migraine.

It will be appreciated that when using a combination of the present invention, both the tachykinin antagonist and rizatriptan will be administered to a patient, within a reasonable period of time. The compounds may be in the same pharmaceutically acceptable carrier and therefore administered simultaneously. They may be in separate pharmaceutical carriers such as intranasal sprays or drops and administered either simultaneously, by mixing the materials just prior to administration or in different dosage forms such as a spray and a tablet which are taken simultaneously. The term "combination" also refers to the case where the compounds are provided in separate dosage forms and are administered sequentially. Therefore, by way of example, the rizatriptan may be administered as an intranasal drop or spray and then within a reasonable period of time, the tachykinin antagonist may be administered either as a intranasal spray, intranasal drop, injection or via an oral dosage form.

By "reasonable period of time" is meant a time period that is not in excess of about 1 hour. That is, for example, if the rizatriptan is provided as intranasal drops, then within one hour, the tachykinin antagonist should be administered, either in the same type of dosage form, or another dosage form which provides effective delivery of the medicament.

The compositions of the present invention are useful for the treatment of migraine. By "migraine" is meant the symptom complex occurring periodically and characterised by pain in the head (usually unilateral), vertigo, nausea and vomiting, photophobia, and scintillating appearances of light (see Steadman's Medical Dictionary, 25th edition).

The compositions of the present invention may also be of use in the treatment of vertigo and nausea such as that associated with Ménière's disease and middle-ear surgery.

The compositions of the present invention are especially useful for the treatment of or prevention of migraine where the use of a 5-HT$_{1B/1D}$ receptor agonist is generally prescribed. By the use of a combination of a tachykinin antagonist and rizatriptan in accordance with the present invention, it is now also possible to treat or prevent migraine attacks in patients for whom conventional 5-HT$_{1B/1D}$ receptor agonist therapy might not be wholly successful or where recurrences of the migraine is prevalent.

The tachykinin antagonists of use in the present invention may be any tachykinin antagonist known from the art. Preferably, the tachykinin antagonist is an NK-1 or NK-2 receptor antagonist, especially an NK-1 receptor antagonist.

NK-1 receptor antagonists of use in the present invention are described in published European Patent Specification Nos. 0 360 390, 0 394 989, 0 429 366, 0 443 132, 0 482 539, 0 512 901, 0 512 902, 0 514 273, 0 514 275, 0 517 589, 0 520 555, 0 522 808, 0 528 495, 0 532 456, 0 533 280, 0 536 817, 0 545 478, 0 577 394, 0 590 152, 0 599 538, 0 610 793, 0 634 402, 0 686 629, 0 693 489, 0 694 535, 0 699 655, 0 699 674, 0 707 006, 0 708 101, 0 714 891, 0 723 959, 0 733 632 and 0 776 893; and in International Patent Specification Nos. 90/05525, 90/05729, 91/09844, 91/18899, 92/01688, 92/06079, 92/12151, 92/15585, 92/17449, 92/20661, 92/20676, 92/21677, 93/00330, 93/00331, 93/01159, 93/01165, 93/01169, 93/01170, 93/06099, 93/09116, 93/10073, 93/14113, 93/18023, 93/19064, 93/21155, 9321181, 93/23380, 93/24465, 94/01402, 94/02461, 94/03429, 94/03445, 94/04494, 94/04496, 94/05625, 94/07843, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 96/22525, 95/23798, 95/26338, 95/28418, 95/30674, 95/30687, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Specification Nos. 2 266 529, 2 268 931, 2 269 170, 2 269 590, 2 271 774, 2 292 144, 2 293 168, 2 293 169, and 2 302 689.

NK-2 receptor antagonists of use in the present invention are described in published European Patent Specification Nos. 0 347 802, 0 428 434, 0 474 561, 0 512 901, 0 515 240 and 0 733 632; and in International Patent Specification Nos. 92/19254 and 93/14084.

Where the tachykinin antagonist used in the combination of the present invention is an NK-1 receptor antagonist, there is the further advantage that the NK-1 receptor antagonist may treat or prevent the nausea and vomiting associated with a migraine attack. The anti-emetic effects of NK-1 receptor antagonists has been reported by, for instance, Bountra et al, Eur. J. Pharmacol., (1993) 249, R$^3$–R$^4$; Tattersall et al, Eur. J. Pharmacol., (1993) 250, R$^5$–R$^6$; and Watson et al, Br. J. Pharmacol., (1995) 115, 84–94.

One class of tachykinin antagonists of use in the present invention is that described in European Patent Specification No. 0 577 394, i.e. compounds of formula (I):

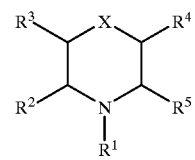

(I)

or a pharmaceutically acceptable salt thereof, wherein:
R$^1$ is selected from the group consisting of:
  (1) hydrogen;
  (2) C$_{1-6}$alkyl, unsubstituted or substituted with one or more of the substituents selected from:
    (a) hydroxy,
    (b) oxo,
    (c) C$_{1-6}$alkoxy,
    (d) phenyl-C$_{1-3}$alkoxy,
    (e) phenyl,
    (f) —CN,
    (g) halo,
    (h) —NR$^9$R$^{10}$, wherein R$^9$ and R$^{10}$ are independently selected from:
      (i) hydrogen,
      (ii) C$_{1-6}$alkyl,
      (iii) hydroxy-C$_{1-6}$alkyl, and
      (iv) phenyl,
    (i) —NR$^9$COR$^{10}$, wherein R$^9$ and R$^{10}$ are as defined above,
    (j) —NR$^9$CO$_2$R$^{10}$, wherein R$^9$ and R$^{10}$ are as defined above,
    (k) —CONR$^9$R$^{10}$, wherein R$^9$ and R$^{10}$ are as defined above,
    (l) —COR$^9$, wherein R$^9$ is as defined above,
    (m) —CO$_2$R$^9$, wherein R$^9$ is as defined above,
    (n) heterocycle, wherein the heterocycle is selected from the group consisting of:
      (A) benzimidazolyl,
      (B) benzofuranyl,
      (C) benzthiophenyl,
      (D) benzoxazolyl,
      (E) furanyl,
      (F) imidazolyl,
      (G) indolyl,
      (H) isoxazolyl,
      (I) isothiazolyl,
      (J) oxadiazolyl,
      (K) oxazolyl,
      (L) pyrazinyl,
      (M) pyrazolyl,
      (N) pyridyl,
      (O) pyrimidyl,
      (P) pyrrolyl,
      (Q) quinolyl,
      (R) tetrazolyl,
      (S) thiadiazolyl,
      (T) thiazolyl,
      (U) thienyl,
      (V) triazolyl,
      (W) azetidinyl,
      (X) 1,4-dioxanyl,
      (Y) hexahydroazepinyl,
      (Z) oxanyl,
      (AA) piperazinyl,
      (AB) piperidinyl,
      (AC) pyrrolidinyl,
      (AD) tetrahydrofuranyl, and (AE) tetrahydrothienyl,
and wherein the heterocylcle is unsubstituted or substituted with one or more substituent(s) selected from:
(i) $C_{1-6}$alkyl, unsubstituted or substituted with halo, —$CF_3$, —$OCH_3$, or phenyl,
(ii) $C_{1-6}$alkoxy,
(iii) oxo,
(iv) hydroxy,
(v) thioxo,
(vi) —$SR^9$, wherein $R^9$ is as defined above,
(vii) halo,
(viii) cyano,
(ix) phenyl,
(x) trifluoromethyl,
(xi) —$(CH_2)_m$—$NR^9R^{10}$, wherein m is 0, 1 or 2, and $R^9$ and $R^{10}$ are as defined above,
(xii) —$NR^9COR^{10}$, wherein $R^9$ and $R^{10}$ are as defined above,
(xiii) —$CONR^9R^{10}$, wherein $R^9$ and $R^{10}$ are as defined above,
(xiv) —$CO_2R^9$, wherein $R^9$ is as defined above, and
(xv) —$(CH_2)_m$—$OR^9$, wherein m and $R^9$ are as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein $R^9$ is as defined above,
(j) —$CO_2R^9$, wherein $R^9$ is as defined above,
(k) heterocycle, wherein the heterocycle is as defined above;
(4) $C_{2-6}$alkynyl;
(5) phenyl, unsubstitued or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —$NO_2$,
(h) —$CF_3$,
(i) —$(CH_2)_m$—$NR^9R^{10}$, wherein m, $R^9$ and $R^{10}$ are as defined above,
(j) —$NR^9COR^{10}$, wherein $R^9$ and $R^{10}$ are as defined above,
(k) —$NR^9CO_2R^{10}$, wherein $R^9$ and $R^{10}$ are as defined above,
(l) —$CONR^9R^{10}$, wherein $R^9$ and $R^{10}$ are as defined above,
(m) —$CO_2NR^9R^{10}$, wherein $R^9$ and $R^{10}$ are as defined above,
(n) —$COR^9$, wherein $R^9$ is as defined above,
(o) —$CO_2R^9$, wherein $R^9$ is as defined above;
$R^2$ and $R^3$ are independently selected from the group consisting of:
(1) hydrogen;
(2) $C_{1-6}$alkyl, unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are independently selected from:
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above, and
(m) —$CO_2R^9$, wherein $R^9$ is as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$ wherein $R^9$ and $R^{10}$ are as defined above,
(i) —$COR^9$, wherein $R^9$ is as defined above,
(j) —$CO_2R^9$, wherein $R^9$ is as defined above;
(4) $C_{2-6}$alkynyl;
(5) phenyl, unsubstituted or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —$NO_2$,
(h) —$CF_3$,
(i) —$(CH_2)m$—$NR^9R^{10}$, wherein m, $R^9$ and $R^{10}$ are as defined above,
(j) —$NR^9COR^{10}$, wherein $R^9$ and $R^{10}$ are as defined above,
(k) —$NR^9CO_2R^{10}$, wherein $R^9$ and $R^{10}$ are as defined above,
(l) —$CONR^9R^{10}$, wherein $R^9$ and $R^{10}$ are as defined above,
(m) —$CO_2NR^9R^{10}$, wherein $R^9$ and $R^{10}$ are as defined above,
(n) —$COR^9$, wherein $R^9$ is as defined above,
(o) —$CO_2R^9$, wherein $R^9$ is as defined above;
and the groups $R^1$ and $R^2$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) oxazolyl, and
(g) thiazolyl,
and wherein the heterocyclic ring is unsubstituted or substituted with one or more substituent(s) selected from:

(i) $C_{1-6}$alkyl,
(ii) oxo,
(iii) $C_{1-6}$alkoxy,
(iv) —$NR^9R^{10}$, wherein $R^9$ and $R^{10}$ are as defined above,
(v) halo, and
(vi) trifluoromethyl;

and the groups $R^2$ and $R^1$ may be joined together to form a carbocyclic ring selected from the group consisting of:
(a) cyclopentyl,
(b) cyclohexyl,
(c) phenyl,
and wherein the carbocyclic ring is unsubstituted or substituted with one or more substituents selected from:
(i) $C_{1-6}$alkyl,
(ii) $C_{1-6}$alkoxy,
(iii) —$NR^9R^{10}$, wherein $R^9$ and $R^{10}$ are as defined above,
(iv) halo, and
(v) trifluoromethyl;

and the groups $R^2$ and $R^3$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl,
and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —$NR^9R^{10}$, wherein $R^9$ and $R^{10}$ are as defined above,
(v) halo, and
(vi) trifluoromethyl;

X is selected from the group consisting of:
(1) —O—,
(2) —S—,
(3) —SO—, and
(4) —$SO_2$—;

$R^4$ is selected from the group consisting of:

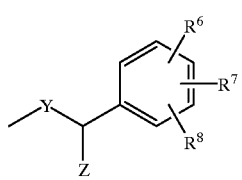

(1)

(2) —Y—$C_{1-6}$alkyl, wherein alkyl is unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above,
(m) —$CO_2R^9$, wherein $R^9$ is as defined above;

(3) —Y—C2-6alkenyl, wherein the alkenyl is unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein R is as defined above,
(j) —$CO_2R^9$, wherein $R^9$ is as defined above, (4) —O(CO)-phenyl, wherein the phenyl is unsubstituted or substituted with one or more of $R^6$, $R^7$ and $R^8$;

$R^5$ is selected from the group consisting of:
(1) phenyl, unsubstituted or substituted with one or more of $R^{11}$, $R^{12}$ and $R^{13}$;
(2) $C_{1-8}$alkyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above,
(m) —$CO_2R^9$, wherein $R^9$ is as defined above;

(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein $R^9$ is as defined above,
(j) —$CO_2R^9$, wherein $R^9$ is as defined above;

(4) heterocycle, wherein the heterocycle is as defined above;

$R^6$, $R^7$ and $R^8$ are independently selected from the group consisting of:
(1) hydrogen;
(2) $C_{1-6}$alkyl, unsubstituted or substituted with one or more of the substituents selected from:
 (a) hydroxy,
 (b) oxo,
 (c) $C_{1-6}$alkoxy,
 (d) phenyl-$C_{1-3}$alkoxy,
 (e) phenyl,
 (f) —CN,
 (g) halo,
 (h) —$NR^9R^{10}$, wherein $R^9$ and $R^{10}$ are as defined above,
 (i) —$NR^9COR^{10}$, wherein $R^9$ and $R^{10}$ are as defined above,
 (j) —$NR^9CO_2R^{10}$, wherein $R^9$ and $R^{10}$ are as defined above,
 (k) —$CONR^9R^{10}$, wherein $R^9$ and $R^{10}$ are as defined above,
 (l) —$COR^9$, wherein $R^9$ is as defined above, and
 (m) —$CO_2R^9$, wherein $R^9$ is as defined above;
(3) $C_{2-6}$alkenyl, unsubstituted or substituted with one or more of the substituent(s) selected from:
 (a) hydroxy,
 (b) oxo,
 (c) $C_{1-6}$alkoxy,
 (d) phenyl-$C_{1-3}$alkoxy,
 (e) phenyl,
 (f) —CN,
 (g) halo,
 (h) —$CONR^9R^{10}$ wherein $R^9$ and $R^{10}$ are as defined above,
 (i) —$COR^9$ wherein $R^9$ is as defined above,
 (j) —$CO_2R^9$, wherein $R^9$ is as defined above;
(4) $C_{2-6}$alkynyl;
(5) phenyl, unsubstituted or substituted with one or more of the substituent(s) selected from:
 (a) hydroxy,
 (b) $C_{1-6}$alkoxy,
 (c) $C_{1-6}$alkyl,
 (d) $C_{2-5}$alkenyl,
 (e) halo,
 (f) —CN,
 (g) —$NO_2$,
 (h) —$CF_3$,
 (i) —$(CH_2)_m$—$NR^9R^{10}$, wherein m, $R^9$ and $R^{10}$ are as defined above,
 (j) —$NR^9COR^{10}$, wherein $R^9$ and $R^{10}$ are as defined above,
 (k) —$NR^9CO_2R^{10}$, wherein $R^9$ and $R^{10}$ are as defined above,
 (l) —$CONR^9R^{10}$, wherein $R^9$ and $R^{10}$ are as defined above,
 (m) —$CO_2NR^9R^{10}$, wherein $R^9$ and $R^{10}$ are as defined above,
 (n) —$COR^9$, wherein $R^9$ is as defined above;
 (o) —$CO_2R^9$, wherein $R^9$ is as defined above;
(6) halo,
(7) —CN,
(8) —$CF_3$,
(9) —$NO_2$,
(10) —$SR^{14}$, wherein $R^{14}$ is hydrogen or $C_{1-5}$alkyl,
(11) —$SOR^{14}$, wherein $R^{14}$ is as defined above,
(12) —$SO_2R^{14}$, wherein $R^{14}$ is as defined above,
(13) $NR^9COR^{10}$, wherein $R^9$ and $R^{10}$ are as defined above,
(14) $CONR^9COR^{10}$, wherein $R^9$ and $R^{10}$ are as defined above,
(15) $NR^9R^{10}$, wherein $R^9$ and $R^{10}$ are as defined above,
(16) $NR^9CO_2R^{10}$, wherein $R^9$ and $R^{10}$ are as defined above,
(17) hydroxy,
(18) $C_{1-6}$alkoxy,
(19) $COR^9$, wherein $R^9$ is as defined above,
(20) $CO_2R^9$, wherein $R^9$ is as defined above,
$R^{11}$, $R^{12}$ and $R^{13}$ are independently selected from the definitions of $R^6$, $R^7$ and $R^8$, or —OX;
Y is selected from the group consisting of:
(1) a single bond,
(2) —O—,
(3) —S—,
(4) —CO—,
(5) —$CH_2$—,
(6) —$CHR^5$—, and
(7) —$CR^{15}R^{16}$—, wherein $R^{15}$ and $R^{16}$ are independently selected from the group consisting of:
 (a) $C_{1-6}$alkyl, unsubstituted or substituted with one or more of the substituents selected from:
  (i) hydroxy,
  (ii) oxo,
  (iii) $C_{1-6}$alkoxy,
  (iv) phenyl-$C_{1-3}$alkoxy,
  (v) phenyl,
  (vi) —CN,
  (vii) halo,
  (viii) —$NR^9R^{10}$, wherein $R^9$ and $R^{10}$ are as defined above,
  (ix) —$NR^9COR^{10}$, wherein $R^9$ and $R^{10}$ are as defined above,
  (x) —$NR^9CO_2R^{10}$, wherein $R^9$ and $R^{10}$ are as defined above,
  (xi) —$CONR^9R^{10}$, wherein $R^9$ and $R^{10}$ are as defined above,
  (xii) —$COR^9$, wherein $R^9$ is as defined above, and
  (xiii) —$CO_2R^9$, wherein $R^9$ is as defined above;
 (b) phenyl, unsubstituted or substituted with one or more of the substituent(s) selected from:
  (i) hydroxy,
  (ii) $C_{1-6}$alkoxy,
  (iii) $C_{1-6}$alkyl,
  (iv) $C_{2-5}$alkenyl,
  (v) halo,
  (vi) —CN,
  (vii) —$NO_2$,
  (viii) —$CF_3$,
  (ix) —$(CH_2)_m$—$NR^9R^{10}$, wherein m, $R^9$ and $R^{10}$ are as defined above,
  (x) —$NR^9COR^{10}$, wherein $R^9$ and $R^{10}$ are as defined above,
  (xi) —$NR^9CO_2R^{10}$, wherein $R^9$ and $R^{10}$ are as defined above,
  (xii) —$CONR^9R^{10}$, wherein $R^9$ and $R^{10}$ are as defined above,
  (xiii) —$CO_2NR^9R^{10}$, wherein $R^9$ and $R^{10}$, are as defined above.
  (xiv) —$COR^9$, wherein $R^9$ is as defined above, and
  (xv) —$CO_2R^9$, wherein $R^9$ is as defined above;
Z is selected from:
(1) hydrogen, (2) C$_{1-4}$alkyl, and
(3) hydroxy, with the proviso that if Y is —O—, Z is other than hydroxy, or if Y is —CHR$^{15}$—, then Z and R$^{15}$ may be joined together to form a double bond.

A particularly preferred compound of formula (I) is 2-(R)-(1-(R)-(3,5-bis(trifluoromethyl)pheny)ethoxy)-3-(S)-(4-fluorophenyl)-4-(3-(5-oxo-1H,4H-1,2,4-triazolo)methyl)morpholine; or a pharmaceutically acceptable salt thereof.

Another class of tachykinin antagonists of use in the present invention are compounds of formula (II):

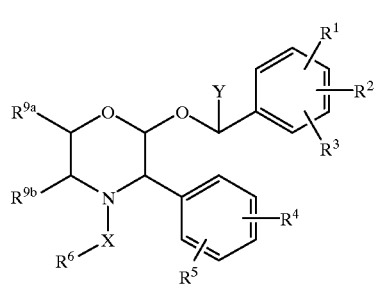

(II)

or a pharmaceutically acceptable salt or prodrug thereof, wherein
R$^1$ is hydrogen, halogen, C$_{1-6}$alkyl, C$_{1-6}$alkoxy, CF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ each independently represent hydrogen or C$_{1-4}$alkyl;
R$^2$ is hydrogen, halogen, C$_{1-6}$alkyl, C$_{1-6}$alkoxy substituted by C$_{1-4}$alkoxy or CF$_3$;
R$^3$ is hydrogen, halogen or CF$_3$;
R$^4$ is hydrogen, halogen, C$_{1-6}$alkyl, C$_{1-6}$alkoxy, CF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ each independently represent hydrogen or C$_{1-4}$alkyl;
R$^5$ is hydrogen, halogen, C$_{1-6}$alkyl, C$_{1-6}$alkoxy substituted by C$_{1-4}$alkoxy or CF$_3$;
R$^6$ is a 5-membered or 6-membered heterocyclic ring containing 2 or 3 nitrogen atoms optionally substituted by =O, =S or a C$_{1-4}$alkyl group, and optionally substituted by a group of the formula ZNR$^7$R$^8$ where Z is C$_{1-6}$alkylene or C$_{3-6}$cycloalkylene;
R$^7$ is hydrogen, C$_{1-4}$alkyl, C$_{3-7}$cycloalkyl or C$_{3-7}$cycloalkylC$_{1-4}$alkyl, or C$_{2-4}$alkyl substituted by C$_{1-4}$alkoxy or hydroxyl;
R$^8$ is hydrogen, C$_{1-4}$alkyl, C$_{3-7}$cycloalkyl or C$_{3-7}$cycloalkylC$_{1-4}$alkyl, or C$_{2-4}$alkyl substituted by one or two substituents selected from C$_{1-4}$alkoxy, hydroxyl or a 4, 5 or 6 membered heteroaliphatic ring containing one or two heteroatoms selected from N, O and S;
or R$^7$, R$^8$ and the nitrogen atom to which they are attached form a heteroaliphatic ring of 4 to 7 ring atoms, optionally substituted by a hydroxy group, and optionally containing a double bond, which ring may optionally contain an oxygen or sulphur ring atom, a group S(O) or S(O)$_2$ or a second nitrogen atom which will be part of a NH or NR$^C$ moiety where R$^c$ is C$_{1-4}$alkyl optionally substituted by hydroxy or C$_{1-4}$alkoxy;
or R$^7$, R$^8$ and the nitrogen atom to which they are attached form a non-aromatic azabicyclic ring system of 6 to 12 ring atoms;

or Z, R$^7$ and the nitrogen atom to which they are attached form a heteroaliphatic ring of 4 to 7 ring atoms which may optionally contain an oxygen ring atom;
R$^{9a}$ and R$^{9b}$ are each independently hydrogen or C$_{1-4}$alkyl, or R$^{9a}$ and R$^{9b}$ are joined so, together with the carbon atoms to which they are attached, there is formed a C$_{5-7}$ ring;
X is an alkylene chain of 1 to 4 carbon atoms optionally substituted by oxo; and
Y is a C$_{1-4}$alkyl group optionally substituted by a hydroxyl group;
with the proviso that if Y is C$_{1-4}$alkyl, R$^6$ is susbstituted at least by a group of formula ZNR$^7$R$^8$ as defined above.

A particularly preferred compound of formula (II) is 2-(R)-(1-(R)-(3,5-bis(trifluoromethyl)phenyl)ethoxy)-4-(5-(dimethylamino)methyl-1,2,3-triazol-4-yl)methyl-3-(S)-(4-fluorophenyl)morpholine; or a pharmaceutically acceptable salt thereof.

Another class of tachykinin antagonists of use in the present invention are those compounds of formula (III):

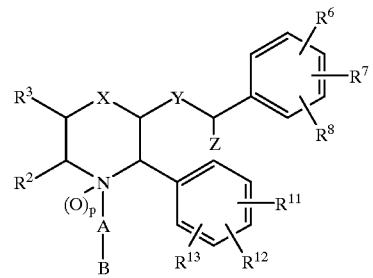

(III)

or a pharmaceutically acceptable salt thereof, wherein:
R$^2$ and R$^3$ are independently selected from the group consisting of:
(1) hydrogen,
(2) C$_{1-6}$alkyl, unsubstituted or substituted with one or more of the substituents selected from:
  (a) hydroxy,
  (b) oxo,
  (c) C$_{1-6}$alkoxy,
  (d) phenyl-C$_{1-3}$alkoxy,
  (e) phenyl,
  (f) —CN,
  (g) halo,
  (h) —NR$^9$R$^{10}$, wherein R$^9$ and R$^{10}$ are independently selected from:
    (I) hydrogen,
    (ii) C$_{1-6}$alkyl,
    (iii) hydroxy-C$_{1-6}$alkyl, and
    (iv) phenyl,
  (i) —NR$^9$COR$^{10}$, wherein R$^9$ and R$^{10}$ are as defined above,
  (j) —NR$^9$CO$_2$R$^{10}$, wherein R$^9$ and R$^{10}$ are as defined above,
  (k) —CONR$^9$R$^{10}$, wherein R$^9$ and R$^{10}$ are as defined above,
  (l) —COR$^9$, wherein R$^9$ is as defined above, and
  (m) —CO$_2$R$^9$, wherein R$^9$ is as defined above;
(3) C$_{2-6}$alkenyl, unsubstituted or substituted with one or more of the substituent(s) selected from:
  (a) hydroxy,
  (b) oxo, (c) $C_{1-6}$alkoxy,
(d) phenyl-$C_{1-3}$alkoxy,
(e) phenyl,
(f) —CN,
(g) halo,
(h) —CONR$^9$R$^{10}$ wherein R$^9$ and R$^{10}$ are as defined above,
(i) —COR$^9$ wherein R$^9$ is as defined above,
(j) —CO$_2$R$^9$, wherein R$^9$ is as defined above;
(4) $C_{2-6}$alkynyl;
(5) phenyl, unsubstituted or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above,
(o) —CO$_2$R$^9$, wherein R$^9$ is as defined above;
and the groups R$^2$ and R$^3$ may be joined together to form a carbocyclic ring selected from the group consisting of:
(a) cyclopentyl,
(b) cyclohexyl,
(c) phenyl,
and wherein the carbocyclic ring is unsubstituted or substituted with one or more substituents selected from:
(i) $C_{1-6}$alkyl,
(ii) $C_{1-6}$alkoxy,
(iii) —NR$^9$R$^{10}$, wherein R$^9$ and R$^{10}$ are as defined above,
(iv) halo, and
(v) trifluoromethyl;
and the groups R$^2$ and R$^3$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl,
and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —NR$^9$R$^{10}$, wherein R$^9$ and R$^{10}$ are as defined above,
(v) halo, and
(vi) trifluoromethyl;
R$^6$, R$^7$ and R$^8$ are independently selected from the group consisting of:
(1) hydrogen;
(2) $C_{1-6}$alkyl, unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above, and
(m) —CO$_2$R$^9$, wherein R$^9$ is as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —CONR$^9$R$^{10}$ wherein R$^9$ and R$^{10}$ are as defined above,
(i) —COR$^9$ wherein R$^9$ is as defined above,
(j) —CO$_2$R$^9$, wherein R$^9$ is as defined above;
(4) $C_{2-6}$alkynyl;
(5) phenyl, unsubstituted or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above,
(o) —CO$_2$R$^9$, wherein R$^9$ is as defined above;
(6) halo,
(7) —CN,
(8) —CF$_3$,
(9) —NO$_2$,
(10) —SR$^{14}$, wherein R$^{14}$ is hydrogen or $C_{1-5}$alkyl,

(11) —SOR$^{14}$, wherein R$^{14}$ is as defined above,

(12) —SO$_2$R$^{14}$, wherein R$^{14}$ is as defined above,

(13) NR$^9$COR$^{10}$, wherein R$^9$ and R$^{10}$ are as defined above,

(14) CONR$^9$COR$^{10}$, wherein R$^9$ and R$^{10}$ are as defined above,

(15) NR$^9$R$^{10}$, wherein R$^9$ and R$^{10}$ are as defined above,

(16) NR$^9$CO$_2$R$^{10}$, wherein R$^9$ and R$^{10}$ are as defined above,

(17) hydroxy,

(18) C$_{1-6}$alkoxy,

(19) COR$^9$, wherein R$^9$ is as defined above,

(20) CO$_2$R$^9$, wherein R$^9$ is as defined above,

(21) 2-pyridyl,

(22) 3-pyridyl,

(23) 4-pyridyl,

(24) 5-tetrazolyl,

(25) 2-oxazolyl, and

(26) 2-thiazolyl;

R$^{11}$, R$^{12}$ and R$^{13}$ are independently selected from the definitions of R$^6$, R$^7$ and R$^8$, or —OX;

A is selected from the group consisting of:

(1) C$_{1-6}$alkyl, unsubstituted or substituted with one or more of the substituents selected from:
   (a) hydroxy,
   (b) oxo,
   (c) C$_{1-6}$alkoxy,
   (d) phenyl-C$_{1-3}$alkoxy,
   (e) phenyl,
   (f) —CN,
   (g) halo, wherein halo is fluoro, chloro, bromo or iodo,
   (h) —NR$^9$R$^{10}$, wherein R$^9$ and R$^{10}$ are as defined above,
   (i) —NR$^9$COR$^{10}$, wherein R$^9$ and R$^{10}$ are as defined above,
   (j) —NR$^9$CO$_2$R$^{10}$, wherein R$^9$ and R$^{10}$ are as defined above,
   (k) —CONR$^9$R$^{10}$, wherein R$^9$ and R$^{10}$ are as defined above,
   (l) —COR$^9$, wherein R$^9$ is as defined above, and
   (m) —CO$_2$R$^9$, wherein R$^9$ is as defined above;

(2) C$_{2-6}$alkenyl, unsubstituted or substituted with one or more of the substituent(s) selected from:
   (a) hydroxy,
   (b) oxo,
   (c) C$_{1-6}$alkoxy,
   (d) phenyl-C$_{1-3}$alkoxy,
   (e) phenyl,
   (f) —CN,
   (g) halo,
   (h) —CONR$^9$R$^{10}$ wherein R$^9$ and R$^{10}$ are as defined above,
   (i) —COR$^9$ wherein R$^9$ is as defined above, and
   (j) —CO$_2$R$^9$, wherein R$^9$ is as defined above; and (3) C$_{2-6}$alkynyl;

B is a heterocycle, wherein the heterocycle is selected from the group consisting of:

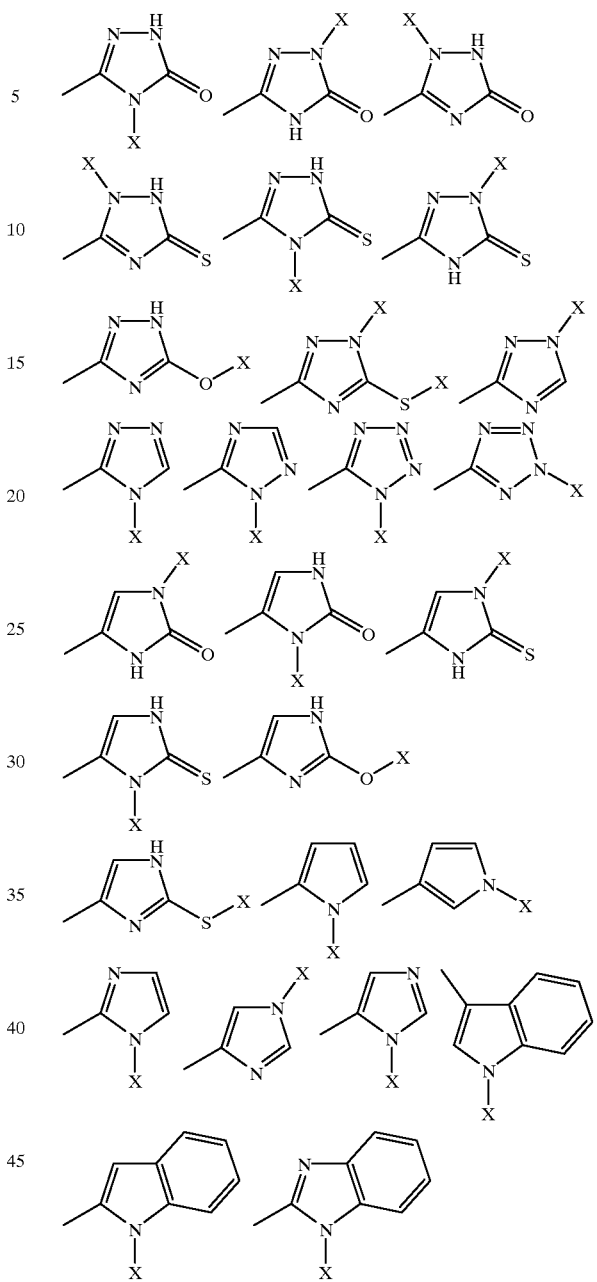

and wherein the heterocycle may be substituted in addition to —X with one or more substituent(s) selected from:

(i) C$_{1-6}$alkyl, unsubstituted or substituted with halo, —CF$_3$, —OCH$_3$, or phenyl, (ii) C$_{1-6}$alkoxy, (iii) oxo, (iv) hydroxy, (v) thioxo, (vi) —SR$^9$, wherein R$^9$ is as defined above, (vii) halo, (viii) cyano, (ix) phenyl, (x) trifluoromethyl, (xi) —(CH$_2$)$_m$—NR$^9$R$^{10}$, wherein m is 0, 1 or 2, and R$^9$ and R$^{10}$ are as defined above, (xii) —NR$^9$COR$^{10}$, wherein R$^9$ and R$^{10}$ are as defined above, (xiii) —CONR$^9$R$^{10}$, wherein R$^9$ and R$^{10}$ are as defined above,
(xiv) —CO$_2$R$^9$, wherein R$^9$ is as defined above, and
(xv) —(CH$_2$)$_m$—OR$^9$, wherein m and R$^9$ are as defined above;

p is 0 or 1;
X is selected from:
(a) —PO(OH)O$^-$.M$^+$, wherein M$^+$ is a pharmaceutically acceptable monovalent counterion,
(b) —PO(O$^-$)$_2$.2M$^+$,
(c) —PO(O$^-$)$_2$.D$^{2+}$, wherein D$^{2+}$ is a pharmaceutically acceptable divalent counterion,
(d) —CH(R$^4$)—PO(OH)O$^-$.M$^+$, wherein R$^4$ is hydrogen or C$_{1-3}$alkyl,
(e) —CH(R$^4$)—PO(O$^-$)$_2$.2M$^+$,
(f) —CH(R$^4$)—PO(O$^-$)$_2$.D$^{2+}$,
(g) —SO$_3^-$.M+,
(h) —CH(R$^4$)—SO$_3^-$.M$^+$,
(i) —CO—CH$_2$CH$_2$—CO$_2^-$.M$^+$,
(j) —CH(CH$_3$)—O—CO—R$^5$, wherein R$^5$ is selected from the group consisting of:

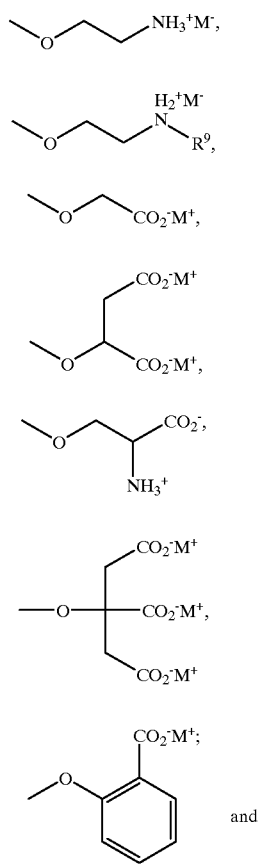

(k) hydrogen, with the proviso that if p is 0 and none of R$^{11}$, R$^{12}$ or R$^{13}$ are —OX, then X is other than hydrogen;

Y is selected from the group consisting of:
(1) a single bond,
(2) —O—,
(3) —S—,
(4) —CO—,
(5) —CH$_2$—,
(6) —CHR$^{15}$—, and
(7) —CR$^{15}$R$^{16}$—, wherein R$^{15}$ and R$^{16}$ are independently selected from the group consisting of:
(a) C$_{1-6}$alkyl, unsubstituted or substituted with one or more of the substituents selected from:
(i) hydroxy,
(ii) oxo,
(iii) C$_{1-6}$alkoxy,
(iv) phenyl-C$_{1-3}$alkoxy,
(v) phenyl,
(vi) —CN,
(vii) halo,
(viii) —NR$^9$R$^{10}$, wherein R$^9$ and R$^{10}$ are as defined above,
(ix) —NR$^9$COR$^{10}$, wherein R$^9$ and R$^{10}$ are as defined above,
(x) —NR$^9$CO$_2$R$^{10}$, wherein R$^9$ and R$^{10}$ are as defined above,
(xi) —CONR$^9$R$^{10}$, wherein R$^9$ and R$^{10}$ are as defined above,
(xii) —COR$^9$, wherein R$^9$ is as defined above, and
(xiii) —CO$_2$R$^9$, wherein R$^9$ is as defined above;
(b) phenyl, unsubstituted or substituted with one or more of the substituent(s) selected from:
(i) hydroxy,
(ii) C$_{1-6}$alkoxy,
(iii) C$_{1-6}$alkyl,
(iv) C$_{2-5}$alkenyl,
(v) halo,
(vi) —CN,
(vii) —NO$_2$,
(viii) —CF$_3$,
(ix) —(CH$_2$)m—NR$^9$R$^{10}$, wherein m, R$^9$ and R$^{10}$ are as defined above,
(x) —NR$^9$COR$^{10}$, wherein R$^9$ and R$^{10}$ are as defined above,
(xi) —NR$^9$CO$_2$R$^{10}$, wherein R$^9$ and R$^{10}$ are as defined above,
(xii) —CONR$^9$R$^{10}$, wherein R$^9$ and R$^{10}$ are as defined above,
(xiii) —CO$_2$NR$^9$R$^{10}$, wherein R$^9$ and R$^{10}$ are as defined above,
(xiv) —COR$^9$, wherein R$^9$ is as defined above, and
(xv) —CO$_2$R$^9$, wherein R$^9$ is as defined above;

Z is selected from:
(1) hydrogen,
(2) C$_{1-6}$alkyl, and
(3) hydroxy, with the proviso that if Y is —O—, Z is other than hydroxy, or if Y is —CHR$^{15}$—, then Z and R$^{15}$ may be joined together to form a double bond.

A particularly preferred compound of formula (II) is 2-(R)-(1-(R)-(3,5-bis(trifluoromethyl)phenyl)ethoxy)-3-(S)-(4-fluorophenyl)-4-(3-(4-monophosphoryl-5-oxo-1H, 4H-1,2,4-triazolo)methyl)morpholine; or a pharmaceutically acceptable salt thereof.

Another class of tachykinin antagonists of use in the present invention is that described in European Patent Specification No. 0 436 334, i.e. compounds of formula (IV):

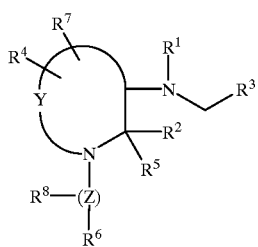

(IV)

or a pharmaceutically acceptable salt thereof, wherein

Y is $(CH_2)_n$ wherein n is an integer from 1 to 4, and wherein any one of the carbon—carbon single bonds in said $(CH_2)_n$ may optionally be replaced by a carbon—carbon double bond, and wherein any one of the carbon atoms of said $(CH_2)_n$ may optionally be substituted with $R^4$, and wherein any one of the carbon atoms of said $(CH_2)_n$ may optionally be substituted with $R^7$;

Z is $(CH_2)_m$ wherein m is an integer from 0 to 6, and wherein any one of the carbon—carbon single bonds of $(CH_2)_m$ may optionally be replaced by a carbon—carbon double bond or a carbon—carbon triple bond, and any one of the carbon atoms of said $(CH_2)_m$ may optionally be substituted with $R^{8-}$;

$R^1$ is hydrogen or $C_{1-8}$alkyl optionally substituted with hydroxy, $C_{1-4}$alkoxy or fluoro;

$R^2$ is a radical selected from hydrogen, $C_{1-6}$ straight or branched alkyl, $C_{3-7}$cycloalkyl wherein one of the $CH_2$ groups in said cycloalkyl may optionally be replaced by NH, oxygen or sulphur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$C_{2-6}$alkyl, benzhydryl and benzyl, wherein each of said aryl and heteroaryl groups and the phenyl moieties of said benzyl, phenyl -$C_{2-6}$alkyl and benzhydryl may optionally be substituted with one or more substituents independently selected from halo, nitro, $C_{1-6}$alkyl, $C_{1-6}$alkoxy, trifluoromethyl, amino, $C_{1-6}$alkylamino, $C_{1-6}$alkyl-O—CO, $C_{1-6}$alkyl-O—CO-$C_{1-6}$alkyl, $C_{1-6}$alkyl-CO—O, $C_{1-6}$alkyl-CO—$C_{1-6}$alkyl-O—, $C_{1-6}$alkyl-CO, $C_{1-6}$alkyl-CO-$C_{1-6}$alkyl-, di-$C_{1-6}$alkylamino, —CONH-$C_{1-6}$alkyl, $C_{1-6}$alkyl-CO—NH-$C_{1-6}$alkyl, —NHCOH and —NHCO-$C_{1-6}$alkyl; and wherein one of the phenyl moieties of said benzhydryl may optionally be replaced by naphthyl, thienyl, furyl or pyridyl;

$R^5$ is hydrogen, phenyl or $C_{1-6}$alkyl;

or $R^2$ and $R^5$ together with the carbon to which they are attached, form a saturated ring having from 3 to 7 carbon atoms wherein one of the $CH_2$ groups in said ring may optionally be replaced by oxygen, NH or sulfur;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of the $(CH_2)$ groups in said cycloalkyl may optionally be replaced by NH, oxygen or sulphur;

wherein each of said aryl and heteroaryl groups may optionally be substituted with one or more substituents, and said $C_{3-7}$cycloalkyl may optionally be substituted with one or two substituents, each of said substituents being independently selected from halo, nitro, $C_{1-6}$alkyl, $C_{1-6}$alkoxy, trifluoromethyl, amino, $C_{1-6}$alkylamino, —CO—NH-$C_{1-6}$alkyl, $C_{1-6}$alkyl-CO—NH-$C_{1-6}$alkyl, —NHCOH and —NHCO-$C_{1-6}$alkyl;

$R^4$ and $R^7$ are each independently selected from hydroxy, halogen, halo, amino, oxo, cyano, methylene, hydroxymethyl, halomethyl, $C_{1-6}$alkylamino, di-$C_{1-6}$alkylamino, $C_{1-6}$-alkoxy, $C_{1-6}$alkyl-O—CO, $C_{1-6}$alkyl-O—CO-$C_{1-6}$alkyl, $C_{1-6}$alkyl-CO—O, $C_{1-6}$alkyl-CO-$C_{1-6}$alkyl-O—, $C_{1-6}$alkyl-CO—, $C_{1-6}$alkyl-CO-$C_{1-6}$alkyl, and the radicals set forth in the definition of $R^2$;

$R^6$ is —NHCOR$^9$, —NHCH$_2$R$^9$, SO$_2$R$^8$ or one of the radicals set forth in any of the definitions of $R^2$, $R^4$ and $R^7$;

$R^8$ is oximino (=NOH) or one of the radicals set forth in any of the definitions of $R^2$, $R^4$ and $R^7$;

$R^9$ is $C_{1-6}$alkyl, hydrogen, phenyl or phenyl$C_{1-6}$alkyl; with the proviso that (a) when m is 0, $R^8$ is absent, (b) when $R^4$, $R^6$, $R^7$ or $R^3$ is as defined in $R^2$, it cannot form together with the carbon to which it is attached, a ring with $R^5$, and (c) when $R^4$ and $R^7$ are attached to the same carbon atom, then either each of $R^4$ and $R^7$ is independently selected from hydrogen, fluoro and $C_{1-6}$alkyl, or $R^4$ and $R^7$, together with the carbon to which they are attached, for a $C_{3-6}$ saturated carbocyclic ring that forms a spiro compound with the nitrogen-containing ring to which they are attached.

A particularly preferred compound of formula (IV) is (2S,3S)-cis-3-(2-methoxybenzylamino)-2-phenylpiperidine; or a pharmaceutically acceptable salt thereof.

Another class of tachykinin antagonists of use in the present invention is that described in International Patent Specification No. WO 93/21155, i.e. compounds of formula (V):

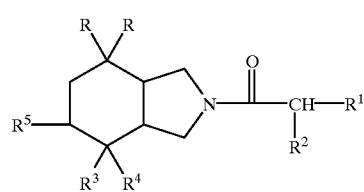

(V)

or a pharmaceutically acceptable salt thereof, wherein radicals R are phenyl radicals optionally 2- or 3-substituted by a halogen atom or a methyl radical;

$R^1$ is optionally substituted phenyl, cyclohexadienyl, naphthyl, indenyl or optionally substituted heterocycle;

$R^2$ is H, halogen, OH, alkyl, aminoalkyl, alkylaminoalkyl, dialkylaminoalkyl, alkyloxy, alkylthio, acyloxy, carboxy, optionally substituted alkyloxycarbonyl, benzyloxycarbonyl, amino or acylamino;

$R^3$ is optionally 2-substituted phenyl;

$R^4$ is OH or fluorine when $R^5$ is H;

or $R^4$ and $R^5$ are OH;

or $R^4$ and $R^5$ together form a bond.

A particularly preferred compound of formula (V) is (3aS,4S,7aS)-7, 7-diphenyl-4-(2-methoxyphenyl)-2-[(2S)-(2-methoxyphenyl)propionyl] perhydroisoindol-4-ol; or a pharmaceutically acceptable salt thereof.

Another class of tachykinin antagonists of use in the present invention is that described in European Patent Specification No. 0 591 040, i.e. compounds of formula (VI):

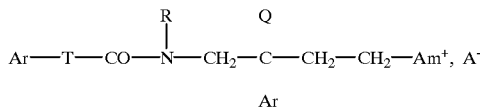

wherein
Ar represents an optionally substituted mono-, di- or tricyclic aromatic or heteroaromatic group;
T represents a bond, a hydroxymethylene group, a $C_{1-4}$alkoxymethylene group or a $C_{1-5}$alkylene group;
Ar' represents a phenyl group which is unsubstituted or substituted by one or more substituents selected from halogen, preferably chlorine or fluorine, trifluoromethyl, $C_{1-4}$alkoxy,-$C_{1-4}$alkyl where the said substituents may be the same or different; a thienyl group; a benzothienyl group; a naphthyl group; or an indolyl group;
R represents hydrogen, $C_{1-4}$alkyl, ($\omega$-$C_{1-4}$alkoxy$C_{1-4}$ alkyl, or $\omega$-$C_{2-4}$alkanoyloxy$C_{2-4}$alkyl;
Q represents hydrogen;
or Q and R together form a 1,2-ethylene, 1,3-propylene or 1,4-butylene group;
Am$^+$ represents the radical

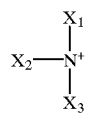

in which $X_1$, $X_2$ and $X_3$, together with the nitrogen atom to which they are attached, form an azabicyclic or azatricyclic ring system optionally substituted by a phenyl or benzyl group; and
A represents a pharmaceutically acceptable anion.

A particularly preferred compound of formula (VI) is (+) 1-[2-[3-(3,4-dichlorophenyl)-1-[(3-isopropoxyphenyl) acetyl] -3-piperidinyl] ethyl]-4-phenyl-1-azabicyclo[2,2,2] octane; or a pharmaceutically acceptable salt, especially the chloride, thereof.

Another class of tachykinin antagonists of use in the present invention is that described in European Patent Specification No. 0 532 456, i.e. compounds of formula (VII):

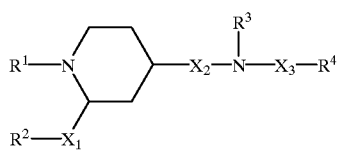

(VII)

or a pharmaceutically acceptable salt thereof, wherein
$R^1$ represents an optionally substituted aralkyl, aryloxyalykl, heteroaralkyl, aroyl, heteroaroyl, cycloalkylcarbonyl, aralkanoyl, heteroarylalkanoyl, aralkoxycarbonyl or arylcarbamoyl group or the acyl group of an $\alpha$-amino acid optionally N-substituted by a lower alkanoyl or carbamoyl-lower alkanoyl group;
$R^2$ represents cycloalkyl or an optionally substituted aryl or heteroaryl group;
$R^3$ represents hydrogen, alkyl, carbamoyl or an alkanoyl or alkenoyl group optionally substituted by carboxy or esterified or amidated carboxy;
$R^4$ represents an optionally substituted aryl group or an optionally partially saturated heteroaryl group;
$X_1$ represents methylene, ethylene, a bond, an optionally ketalised carbonyl group or an optionally etherified hydroxymethylene group;
$X_2$ represents alkylene, carbonyl or a bond; and
$X_3$ represents carbonyl, oxo-lower alkyl, oxo(aza)-lower alkyl, or an alkyl group optionally substituted by phenyl, hydroxymethyl, optionally esterified or amidated carboxy, or (in other than the $\alpha$-position) hydroxy.

A particularly preferred compound of formula (VII) is (2R*,4S*)-2-benzyl-1-(3,5-dimethylbenzoyl)-N-(4-quinolinylmethyl)-4-piperidineamine; or a pharmaceutically acceptable salt thereof.

Another class of tachykinin antagonists of use in the present invention is that described in European Patent Specification No. 0 443 132, i.e. compounds of formula (VIII)

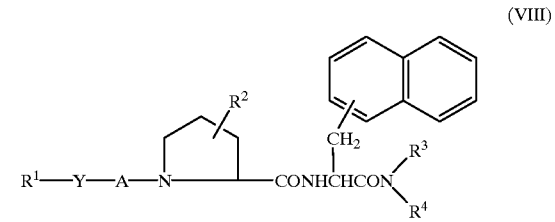

(VIII)

wherein $R^1$ is aryl, or a group of the formula:

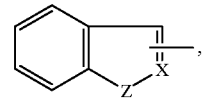

or a pharmaceutically acceptable salt thereof, wherein
X is CH or N; and
Z is O or N—$R^5$, in which $R^5$ is hydrogen or lower alkyl;
$R^2$ is hydroxy or lower alkoxy;
X $R^3$ is hydrogen or optionally substituted lower alkyl;
$R^4$ is optionally substituted ar(lower)alkyl;
A is carbonyl or sulfonyl; and
Y is a bond or lower alkenylene.

A particularly preferred compound of formula (VIII) is the compound of formula (VIIIa)

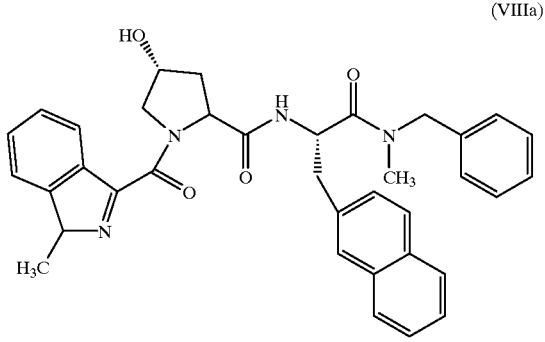

(VIIIa)

or a pharmaceutically acceptable salt thereof.

Another class of tachykinin antagonists of use in the present invention is that described in International Patent Specification No. WO 95/08549, i.e. compounds of formula (IX):

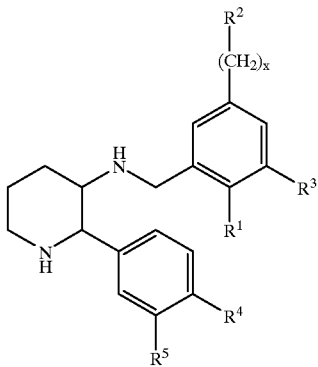

(IX)

wherein $R^1$ is a $C_{1-4}$alkoxy group;
$R^2$ is

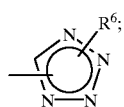

$R^3$ is a hydrogen or halogen atom;
$R^4$ and $R^5$ may each independently represent a hydrogen or halogen atom, or a $C_{1-4}$alkyl, $C_{1-4}$alkoxy or trifluoromethyl group;
$R^6$ is a hydrogen atom, a $C_{1-4}$alkyl, $(CH_2)_m$cyclopropyl, —S(O)$_n C_{1-4}$alkyl, phenyl, $NR^7R^8$, $CH_2C(O)CF_3$ or trifluoromethyl group;
$R^7$ and $R^8$ may each independently represent a hydrogen atom, or a $C_{1-4}$alkyl or acyl group;
x represents zero or 1;
n represents zero, 1 or 2;
mn represents zero or 1;
and pharmaceutically accept able salts and solvates thereof.

Particularly preferred compounds of formula (IX) are (2S,3S)-2-methoxy-5-tetrazol-1-yl-benzyl-(2-phenyl-piperidin-3-yl)-amine, and (2S,3S)-2-methoxy-5-(5-trifluoromethyl-tetrazol-1-yl)-benzyl-(2-phenyl-piperidin-3-yl)-amine, or a pharmaceutically acceptable salt thereof.

Another class of tachykinin antagonists of use in the present invention is that described in International Patent Specification No. WO 95/14017, i.e. compounds of formula (X)

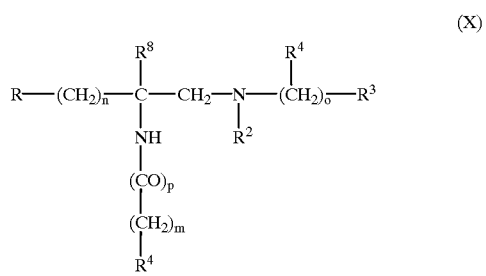

(X)

or a pharmaceutically acceptable salt thereof, wherein
m is zero, 1, 2 or 3;
n is zero or 1;
o is zero, 1 or 2;
p is zero or 1;
R is phenyl, 2- or 3-indolyl, 2- or 3-indolinyl, benzothienyl, benzofuranyl, or naphthyl;
which R groups may be substituted with one or two halo, $C_{1-3}$alkoxy, trifluoromethyl, $C_{1-4}$alkyl, phenyl-$C_{1-3}$alkoxy, or $C_{1-4}$alkanoyl groups;
$R^1$ is trityl, phenyl, diphenylmethyl, phenoxy, phenylthio, piperazinyl, piperidinyl, pyrrolidinyl, morpholinyl, indolinyl, indolyl, benzothienyl, hexamethyleneiminyl, benzofuranyl, tetrahydropyridinyl, quinolinyl, isoquinolinyl, reduced quinolinyl, reduced isoquinolinyl, phenyl-($C_{1-4}$alkyl)-, phenyl-($C_{1-4}$alkoxy)-, quinolinyl-($C_{1-4}$alkyl)-, isoquinolinyl-($C_{1-4}$alkyl)-, reduced quniolinyl-($C_{1-4}$alkyl)-, reduced isoquinolinyl-($C_{1-4}$alkyl)-, benzoyl-($C_{1-3}$alkyl)-, $C_{1-4}$alkyl, or —NH—CH$_2$—$R^5$;
any one of which $R^1$ groups may be substituted with halo, $C_{1-4}$alkyl, $C_{1-4}$alkoxy, trifluoromethyl, amino, $C_{1-4}$alkylamino, di($C_{1-4}$alkyl)amino, or $C_{2-4}$alkanoylamino;
or any one of which $R^1$ groups may be substituted with phenyl, piperazinyl, $C_{3-8}$cycloalkyl, benzyl, $C_{1-4}$alkyl, piperidinyl, pyridinyl, pyrimidinyl, $C_{2-6}$alkanoylamino, pyrrolidinyl, $C_{2-6}$alkanoyl, or $C_{1-4}$alkoxycarbonyl;
any one of which groups may be substituted with halo, $C_{1-4}$alkyl, $C_{1-4}$alkoxy, trifluoromethyl, amino, $C_{1-4}$alkylamino, di($C_{1-4}$alkyl)amino, or $C_{2-4}$alkanoylamino;
or $R^1$ is amino, a leaving group, hydrogen, $C_{1-4}$alkylamino, or di($C_{1-4}$alkyl)amino;
$R^5$ is pyridyl, anilino-($C_{1-3}$alkyl)-, or anilinocarbonyl;
$R^2$ is hydrogen, $C_{1-4}$alkyl, $C_{1-4}$alkylsulfonyl, carboxy-($C_{1-3}$alkyl)-, $C_{1-3}$alkoxycarbonyl-($C_{1-3}$alkyl)-, or —CO—$R^6$;
$R^6$ is hydrogen, $C_{1-4}$alkyl, $C_{1-3}$haloalkyl, phenyl, $C_{1-3}$alkoxy, $C_{1-3}$hydroxyalkyl, amino, $C_{1-4}$alkylamino, di($C_{1-4}$alkyl)amino, or —(CH$_2$)$_q$—$R^7$;
q is zero to 3;
$R^7$ is carboxy, $C_{1-4}$alkoxycarbonyl, $C_{1-4}$alkylcarbonyloxy, amino, $C_{1-4}$alkylamino, di($C_{1-4}$alkyl)amino, $C_{1-6}$alkoxycarbonylamino, or phenoxy, phenylthio, piperazinyl, piperidinyl, pyrrolidinyl, morpholinyl, indolinyl, indolyl, benzothienyl, benzofuranyl, quinolinyl, phenyl-($C_{1-4}$alkyl)-, quinolinyl-($C_{1-4}$ alkyl)-, isoquinolinyl-($C_{1-4}$alkyl)-, reduced quinolinyl-($C_{1-4}$alkyl)-, reduced isoquinolinyl-($C_{1-4}$alkyl)-, benzoyl-$C_{1-3}$alkyl;

any one of which aryl or heterocyclic $R^7$ groups may be substituted with halo, trifluoromethyl, $C_{1-4}$alkoxy, $C_{1-4}$alkyl, amino, $C_{1-4}$alkylamino, di($C_{1-4}$alkyl)amino, or $C_{2-4}$alkanoylamino;

or any one of which $R^7$ groups may be substituted with phenyl, piperazinyl, $C_{3-8}$cycloalkyl, benzyl, piperidinyl, pyridinyl, pyrimidinyl, pyrrolidinyl, $C_{2-6}$alkanoyl, or $C_{1-4}$alkoxycarbonyl;

any of which groups may be substituted with halo, trifluoromethyl, amino, $C_{1-4}$alkoxy, $C_{1-4}$alkyl, $C_{1-4}$alkylamino, di($C_{1-4}$alkyl)amino, or $C_{2-4}$alkanoylamino;

$R^8$ is hydrogen or $C_{1-6}$alkyl;

$R^3$ is phenyl, phenyl-($C_{1-6}$alkyl)-, $C_{3-8}$cycloalkyl, $C_{5-8}$cycloalkenyl, $C_{1-8}$alkyl, naphthyl, $C_{2-8}$alkenyl, or hydrogen;

any one or which groups except hydrogen may be substituted with one or two halo, $C_{1-3}$alkoxy, $C_{1-3}$alkylthio, nitro, trifluoromethyl, or $C_{1-3}$alkyl groups; and $R^4$ is hydrogen or $C_{1-3}$alkyl;

with the proviso that if $R^1$ is hydrogen or halo, $R^3$ is phenyl, phenyl-($C_{1-6}$alkyl)-, $C_{3-8}$cycloalkyl, $C_{5-8}$cycloalkenyl, or naphthyl.

A particularly preferred compound of formula (X) is [N-(2-methoxybenzyl)acetylamino]-3-(1H-indol-3-yl)-2-[N-(2-(4-piperidin-1-yl)piperidin-1-yl)acetylamino] propane; or a pharmaceutically acceptable salt thereof Another class of tachykinin antagonist of use in the present invention is described in International Specification No. WO 93/00331, i.e. compounds of formula (XI):

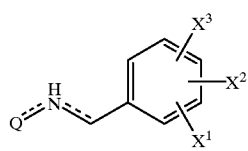

(XI)

wherein $X^1$ is hydrogen, ($C_{1-10}$)alkoxy optionally substituted with from one to three fluorine atoms or ($C_{1-10}$)alkyl optionally substituted with from one to three fluorine atoms;

$X^2$ and $X^3$ are independently selected from hydrogen, halo, nitro, ($C_{1-10}$)alkyl optionally substituted with from one to three fluorine atoms, ($C_{1-10}$)alkoxy optionally substituted with from one to three flourine atoms, trifluoromethyl, hydroxy, phenyl, cyano, amino, ($C_{1-6}$) alkylamino, di-($C_{1-6}$)alkylamino, —C(O)—NH-($C_{1-6}$) alkyl, ($C_{1-6}$)alkyl-C(O)—NH-($C_{1-6}$)alkyl, hydroxy ($C_{1-4}$) alkyl, ($C_{1-4}$)alkoxy($C_{1-4}$)alkyl, —NHC(O)H and —NHC(O)-($C_{1-6}$)alkyl; and Q is a group of formula

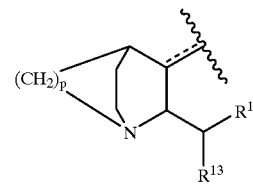
A

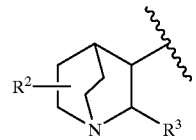
B

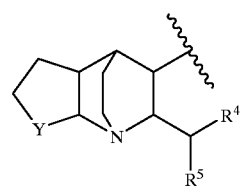
C

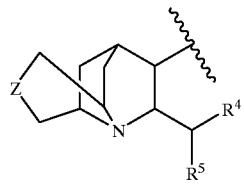
D

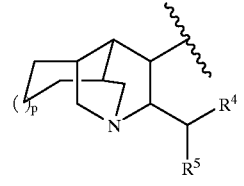
E

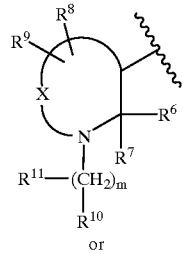
F or

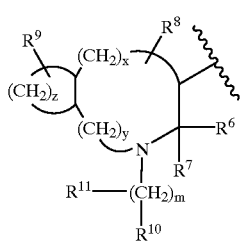
G wherein $R^1$ is a radical selected from furyl, thienyl, pyridyl, indolyl, biphenyl and phenyl optionally substituted with one or two substituents independently selected from halo, ($C_{1-10}$)alkyl optionally substituted with from one to three fluorine atoms, ($C_{1-10}$)alkoxy optionally substituted with from one to three fluorine atoms, carboxy, benzyloxycarbonyl and $(C_{1-3})$alkoxy-carbonyl;

$R^{13}$ is selected from $(C_{3-4})$ branched alkyl, $(C_{5-6})$ branched alkenyl, $(C_{5-7})$cyloalkyl, and the radicals named in the definition of $R^1$;

$R^2$ is hydrogen or $(C_{1-6})$alkyl;

$R^3$ is phenyl, biphenyl, naphthyl, pyridyl, benzhydryl, thienyl or furyl, and $R^3$ may optionally be substituted with from one to three substituents independently selected from halo, $(C_{1-10})$alkyl optionally substituted with from one to three fluorine atoms and $(C_{1-10})$alkoxy optionally substituted with from one to three fluorine atoms;

Y is $(CH_2)_l$ wherein 1 is an integer from one to three, or Y is a group of the formula

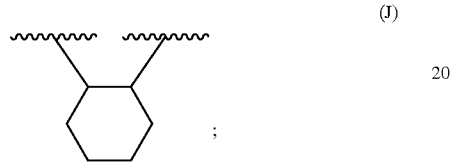

(J)

Z is oxygen, sulfur, amino, $(C_{1-3})$alkylamino or $(CH_2)_n$ wherein n is zero, one or two;

o is two or three;

p is zero or one;

$R^4$ is furyl, thienyl, pyridyl, indolyl, biphenyl, or phenyl optionally substituted with one or two substituents independently selected from halo, $(C_{1-10})$alkyl optionally substitute d with from one to three fluorine atoms, $(C_{1-10})$ alkoxy optionally substituted with from one to three fluorine atoms, carboxy, $(C_{1-3})$alkoxy-carbonyl and benzyloxycarbonyl;

$R^5$ is thienyl, biphenyl or phenyl optionally substituted with one or two substituents independently selected from halo, $(C_{1-10})$alkyl optionally substituted with from one to three fluorine atoms and $(C_{1-10})$alkoxy optionally substituted with from one to three fluorine atoms;

each of the two dashed lines in formula (XI) and the dashed line in formula A represent an optional double bond that may optionally exist when Q is a group of the formula A;

X is $(CH_2)_q$ wherein q is an integer from 1 to 6, and wherein any one of the carbon—carbon single bonds in said $(CH_2)_q$ may optionally be replaced by a carbon—carbon double bond, and wherein any one of the carbon atoms of said $(CH_2)_q$ may optionally be substituted with $R^8$, and wherein any one of the carbon atoms of said $(CH_2)_q$ may optionally be substituted with $R^9$;

m is an integer from 0 to 8, and any one of the carbon—carbon single bonds of $(CH_2)_m$ may optionally be replaced by a carbon—carbon double bond or a carbon—carbon triple bond, and any one of the carbon atoms of said $(CH_2)_m$ may optionally be substituted with $R^{11}$;

$R^6$ is a radical selected from hydrogen, $(C_{1-6})$ straight or branched alkyl, $(C_{3-7})$cycloalkyl wherein one of the carbon atoms may optionally be replaced by nitrogen, oxygen or sulfur; aryl selected from biphenyl, phenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl-$(C_{2-6})$alkyl, benzhydryl and benzyl, wherein each of said aryl and heteroaryl groups and the phenyl moieties of said benzyl, phenyl-$(C_{2-6})$alkyl and benzhydryl may optionally be substituted with one or more substituents independently selected from halo, nitro, $(C_{1-10})$alkyl optionally substituted with from one to three fluorine atoms, $(C_{1-6})$alkoxy optionally substituted with from one to three fluorine atoms, amino, hydroxy-$(C_{1-6})$ alkylamino, $(C_{1-6})$alkoxy$(C_{1-6})$alkyl, $(C_{1-6})$alkylamino, $(C_{1-6})$alkyl-O—C(O)—, $(C_{1-6})$alkyl-O—C(O)-$(C_{1-6})$ alkyl, $(C_{1-6})$alkyl-C(O)—O—, $(C_{1-6})$alkyl-C(O)-$(C_{1-6})$ alkyl-O—, $(C_{1-6})$alkyl-C(O)—, $(C_{1-6})$alkyl-C(O)-$(C_{1-6})$ alkyl-, di-$(C_{1-6})$alkylamino, —C(O)NH-$(C_{1-6})$ alkyl, $(C_{1-6})$alkyl-C(O)—NH-$(C_{1-6})$alkyl, —NHC(O)H and —NHC(O)-$(C_{1-6})$alkyl; and wherein one of the phenyl moieties of said benzhydryl may optionally be replaced by naphthyl, thienyl, furyl or pyridyl;

$R^7$ is hydrogen, phenyl or $(C_{1-6})$alkyl;

or $R^6$ and $R^7$, together with the carbon to which they are attached, form a saturated carbocyclic ring having from 3 to 7 carbon atoms wherein one of said carbon atoms may optionally be replaced by oxygen, nitrogen or sulfur;

$R^8$ and $R^9$ are each independently selected from hydrogen, hydroxy, halo, amino, oxo (=O), nitrile, hydroxy-$(C_{1-6})$alkyl, $C_{1-6}$alkoxy$(C_{1-6})$alkyl, $(C_{1-6})$ alkylamino, di-$(C_{1-6})$alkylamino, $(C_{1-6})$alkoxy, $(C_{1-6})$ alkyl-O—C(O)—, $(C_{1-6})$alkyl-O—C(O)-$(C_{1-6})$alkyl, $(C_{1-6})$alkyl-C(O)—O—, $(C_{1-6})$alkyl-C(O)-$(C_{1-6})$alkyl-O—, $(C_{1-6})$alkyl-C(O)—, $(C_{1-6})$alkyl-C(O)-$(C_{1-6})$ alkyl-, and the radicals set forth in the definition of $R^6$;

$R^{10}$ is $NHCR^{12}$, $NHCH_2R^{12}$, $NHSO_2R^{12}$ or one of the radicals set forth in any of the definitions of $R^6$, $R^8$ and $R^9$;

$R^{11}$ is oximino (=NOH) or one of the radicals set forth in any of the definitions of $R^6$, $R^8$ and $R^9$; and $R^{12}$ is $(C_{1-6})$alkyl, hydrogen, phenyl$(C_{1-6})$alkyl or phenyl optionally substituted with $(C_{1-6})$alkyl; and with the proviso that (a) when m is 0, $R^{11}$ is absent, (b) neither $R^8$, $R^9$, $R^{10}$ nor $R^{11}$ can form, together with the carbon to which it is attached, a ring with $R^7$, (c) when Q is a group of the formula VIII, $R^8$ and $R^9$ cannot be attached to the same carbon atom, (d) when $R^8$ and $R^9$ are attached to the same carbon atom, then either each of $R^8$ and $R^9$ is independently selected from hydrogen, fluoro, $(C_{1-6})$alkyl, hydroxy$(C_{1-6})$alkyl and $(C_{1-6})$ alkoxy$(C_{1-6})$alkyl, or $R^8$ and $R^9$, together with the carbon to which they are attached, form a $(C_{3-6})$ saturated carbocyclic ring that forms a spiro compound with the nitrogen-containing ring to which they are attached, (e) the nitrogen of formula (XI) cannot be double bonded to both Q and the substituted benzyl group to which it is attached, (f) when Q is a group of the formula F and q is 2 and either $R^8$ or $R^9$ is 5-hydroxy$(C_{1-6})$alkyl or 5-$(C_{1-6})$alkoxy$(C_{1-6})$alkyl, then the other of $R^8$ and $R^9$ is either 5 -$(C_{1-3})$alkyl or hydrogen; (g) when Q is a group of the formula F and q is 2, then neither $R^8$ nor $R^9$ is 4-hydroxy$(C_{1-6})$alkyl or 4-$(C_{1-6})$alkoxy$(C_{1-6})$alkyl, and (h) when neither $X^1$, $X^2$ nor $X^3$ is a fluorinated alkoxy group, at least one of $R^1$, $R^3$, $R^4$, $R^5$, $R^6$, $R^7$ and $R^{13}$ is an aryl group substituted with a fluorinated alkoxy group.

A particularly preferred compound of formula (XI) is (2S,3S)-3-(2-methoxy-5-trifluoromethoxybenzyl)amino-2-phenylpiperidine, or a pharmaceutically acceptable salt thereof.

Another class of tachykinin antagonist of use in the present invention is that described in International Specification No. WO 96/21661, i.e. compounds of formula (XII)

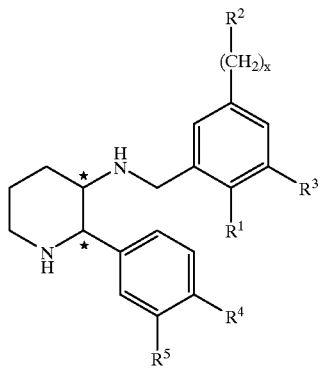
(XII)

wherein
$R_1$ is —O—$(CH_2)p(C_{3-7})$cycloalkyl, —O—$(C_{1-7})$fluoroalkyl, or —O—$(CH_2)_nX$;
$R^2$ is

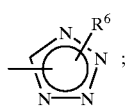

$R^3$ is a hydrogen or halogen atom;
$R^4$ and $R^5$ may each independently represent a hydrogen or halogen atom, or a $C_{1-4}$alkyl, $C_{1-4}$alkoxy or trifluoromethyl group;
X is selected from C(O)—$NR^7R^8$, C(O)$R^9$, $NR^7R^8$, $SO_2NR^7R^8$, $NHSO_2R^9$, $S(O)_sR^9$, $OC_{1-4}$alkyl, $NO_2$, $CO_2H$, $CO_2C_{1-4}$alkyl, CN or, when n is 2, X may also represent OH, SH or $NH_2$;
$R^6$ is a hydrogen atom, a $C_{1-4}$alkyl, $(CH_2)_m$cyclopropyl, —S(O)s($C_{1-4}$)alkyl, phenyl, $NR^{10}R^{11}$, $CH_2C(O)CF_3$, trifluoromethyl, difluoromethyl or cyano group;
$R^7$ and $R^8$ may each independently represent hydrogen atoms or a $C_{1-4}$alkyl group;
$R^9$ represents a $C_{1-4}$alkyl or trifluoromethyl group;
$R^{10}$ and $R^{11}$ may each independently represent a hydrogen atom, or a $C_{1-4}$alkyl or acyl group;
x represents zero or 1;
n represents 1 or 2;
s represents zero, 1 or 2;
m represents zero or 1;
p represents zero or 1;
and pharmaceutically acceptable salts and solvates thereof.

A particularly preferred compounds of formula (XII) is [2-(2-methoxy-1-ethoxy)-5-(5-trifluoromethyl-tetrazol-1-yl)-benzyl]-([2S,3S]-2-phenylpiperidin-3-yl)amine, or a pharmaceutically acceptable salt thereof.

Unless otherwise defined herein, suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl, n-butyl, sec-butyl and tert-butyl.

Unless otherwise defined herein, suitable alkenyl groups include straight-chained and branched alkenyl groups containing from 2 to 6 carbon atoms. Typical examples include vinyl and allyl groups.

Unless otherwise defined herein, suitable alkynyl groups include straight-chained and branched alkynyl groups containing from 2 to 6 carbon atoms. Typical examples include ethynyl and propargyl groups.

Unless otherwise defined herein, suitable cycloalkyl groups include groups containing from 3 to 7 carbon atoms. Particular cycloalkyl groups are cyclopropyl and cyclohexyl.

Unless otherwise defined herein, suitable aryl groups include phenyl and naphthyl groups.

A particular aryl-$C_{1-6}$alkyl, e.g. phenyl-$C_{1-6}$alkyl, group is benzyl.

Unless otherwise defined herein, suitable heteroaryl groups include pyridyl, quinolyl, isoquinolyl, pyridazinyl, pyrimidinyl, pyrazinyl, pyranyl, furyl, benzofuryl, thienyl, benzthienyl, imidazolyl, oxadiazolyl and thiadiazolyl groups.

The term "halogen" as used herein includes fluorine, chlorine, bromine and iodine.

The compounds of use in this invention may have one or more asymmetric centres and can therefore exist as enantiomers and possibly as diastereoisomers. It is to be understood that the present invention relates to the use of all such isomers and mixtures thereof.

Suitable pharmaceutically acceptable salts of the tachykinin antagonists of use in the present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, phosphoric acid or sulphuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

Suitable pharmaceutically acceptable salts of the rizatriptan of use in the present invention include those salts described above in relation to the salts of tachykinin antagonists.

Preferred salts of rizatriptan of use in the present invention include the benzoate and sulfate salts.

As stated above, the tachykinin antagonist and rizatriptan may be formulated in a single pharmaceutical composition or alternatively in individual pharmaceutical compositions for simultaneous, separate or sequential use in accordance with the present invention.

Preferably the compositions according to the present invention are in unit dosage forms such as tablets, pills, capsules, powders, granules, solutions or suspensions, or suppositories, for oral, parenteral or rectal administration, by inhalation or insufflation or administration by trans-dermal patches or by buccal cavity adsorption wafers.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Preferred compositions for administration by injection include those comprising a tachykinin antagonist, as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid , Liposyn™, Infonutrol™, Lipofundin™ and Lipiphysan™. The active ingredient may be either dissolved in a premixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5$\mu$m, and have a pH in the range of 5.5 to 8.0.

Particularly preferred emulsion compositions are those prepared by mixing a tachykinin antagonist with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

The present invention further provides a process for the preparation of a pharmaceutical composition comprising a tachykinin antagonist and rizatriptan, which process comprises bringing a tachykinin antagonist and rizatriptan into association with a pharmaceutically acceptable carrier or excipient.

When administered in combination, either as a single or as separate pharmaceutical composition(s), the tachykinin antagonist and rizatriptan are presented in a ratio which is consistent with the manifestation of the desired effect. In particular, the ratio by weight of the tachykinin antagonist to rizatriptan will suitably be approximately 1 to 1. Preferably this ratio will be between 0.001 to 1 and 1000 to 1, and especially between 0.01 to 1 and 100 to 1.

A suitable dosage level for the tachykinin antagonist is about 0.05 to 1500 mg per day, preferably about 0.25 to 1500 mg per day, and especially about 0.25 to 500 mg/kg per day. The compounds may be administered on a regimen of up to 6 times per day, preferably 1 to 4 times per day.

A suitable oral dosage level for the rizatriptan is about 0.5 to 1500 mg per day, preferably about 2.5 to 1000 mg per day, and especially about 2.5 to 500 mg per day. The compounds may be administered on a regimen of up to 6 times per day, preferably 1 to 4 times per day.

When the sulfate salt of rizatriptan is used, the preferred unit dosage is from about 0.1 mg to about 100 mg, or more preferably from about 1 to about 60 mg and most preferably from about 1 to about 35 mg of rizatriptan sulfate administered in a single dose to one nostril. This dosage is most preferably delivered using a pharmaceutically acceptable intranasal carrier which ranges in volume from about 0.1 mL to about 1.0 mL.

In one embodiment of this invention, the tachykinin antagonist is administered as an oral dosage form or by injection and the rizatriptan is provided in an intranasal formulation containing from about 2% to about 15% of rizatriptan. The preferred regimen requires the delivery of from about 0.1 to about 1.0 mL of such an intranasal formulation to be delivered to the inside of one nostril.

In an other preferred embodiment of this invention, the tachykinin antagonist is delivered as an oral dosage form or by injection while rizatriptan (and in particular rizatriptan benzoate) is delivered using a fast dissolving oral formulation. By a "fast dissolving oral formulation" is meant, an oral delivery form which when placed on the tongue of a patient, dissolves within about 10 seconds.

Other preferred embodiments include the delivery of the tachykinin antagonist using an oral dosage form or by injection and the delivery of the rizatriptan as a conventional tablet, liquid, elixir or suspension. 5-HT$_{1D}$ agonists have a systemic mechanism of action. While the rate of headache recurrence with 5-HT$_{1D}$ agonists is approximately 40% within a 24 hour period, the overall recurrence rate will decrease when a tachykinin antagonist and rizatriptan are administered together in the treatment of migraine, since the combination will affect the migraine in two different ways. Firstly, the rizatriptan will lessen the signals to the sensory nerves. Secondly, simultaneously, the tachykinin antagonist will block inflammation around blood vessels in sensitive tissues such as the dura mater. Since the pathogenic circle in migraine is influenced by these two major mechanisms, the chances for headache relapse decrease. When a tachykinin antagonist and rizatriptan are both used in the treatment of migraine, both mechanisms will be suppressed and the duration of action in the treatment of migraine will therefore be increased.

It will be appreciated that the amount of a tachykinin antagonist and rizatriptan required for use in the treatment or prevention of migraine will vary not only with the particular compounds or compositions selected but also with the route of administration, the nature of the condition being treated, and the age and condition of the patient, and will ultimately be at the discretion of the patient's physician or pharmacist.

The compounds of formulae (I), (II), (III), (IV), (V), (VI), (VII), (VIII), (IX), (X), (XI) and (XII) may be prepared by the methods described in EP-A-0 577 394 (or WO 95/16679), WO 95/18124, WO 95/23798, EP-A-0 436 334, WO 93/21155, EP-A-0 591 040, EP-A-0 532 456, EP-A-0 443 132, WO 95/08549, WO 95/14017, WO 93/00331 and WO 96/21661, respectively.

The following examples illustrate pharmaceutical compositions according to the invention.

These formulations may be prepared with separate active ingredients or with a combination of active ingredients in one composition. In such combined preparations, the ratio of tachykinin antagonist to rizatriptan will depend upon the choice of active ingredients.

EXAMPLE 1A
Tablets containing 2-20 mg of the NK-1 antagonist and 5–10 mg of rizatriptan

| | Amount mg | | | |
|---|---|---|---|---|
| NK-1 antagonist | 2.0 | 2.0 | 20.0 | 20.0 |
| rizatriptan | 5.0 | 10.0 | 5.0 | 10.0 |
| Microcrystalline cellulose | 20.0 | 20.0 | 20.0 | 20.0 |
| Modified food corn starch | 20.0 | 20.0 | 20.0 | 20.0 |
| Lactose | 52.5 | 47.5 | 34.5 | 29.5 |
| Magnesium Stearate | 0.5 | 0.5 | 0.5 | 0.5 |

EXAMPLE 1B
Tablets containing 26–100 mg of the NK-1 antagonist and 5–10 mg of rizatriptan

| | Amount mg | | | | | |
|---|---|---|---|---|---|---|
| NK-1 antagonist | 26.0 | 26.0 | 40.0 | 40.0 | 100.0 | 100.0 |
| rizatriptan | 5.0 | 10.0 | 5.0 | 10.0 | 5.0 | 10.0 |
| Microcrystalline cellulose | 80.0 | 80.0 | 80.0 | 80.0 | 80.0 | 80.0 |
| Modified food corn starch | 80.0 | 80.0 | 80.0 | 80.0 | 80.0 | 80.0 |
| Lactose | 208.5 | 203.5 | 194.5 | 189.5 | 134.5 | 129.5 |
| Magnesium Stearate | 0.5 | 0.5 | 0.5 | 0.5 | 0.5 | 0.5 |

The active ingredients cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 2.0 mg, 20.0 mg, 26.0 mg, 40.0 mg and 100 mg of the NK-1 receptor antagonist and 5.0 mg or 10.0 mg of rizatriptan per tablet.

EXAMPLE 2
Parenteral injection

| | Amount mg | |
|---|---|---|
| NK-1 antagonist | 20.0 | 40.0 |
| rizatriptan | 50.0 | 50.0 |
| Citric Acid Monohydrate | 0.75 | 0.75 |
| Sodium Phosphate | 4.5 | 4.5 |
| Sodium Chloride | 9.0 | 9.0 |
| Water for injection | to 10 ml | to 10 ml |

The sodium phosphate, citric acid monohydrate and sodium chloride are dissolved in a portion of the water. The active ingredients are dissolved or suspended in the solution and made up to volume.

EXAMPLES 3–6

Intranasal Formulation Containing Rizatriptan
Sterile Intranasal Formulation

| | Example 3 | Example 4 |
|---|---|---|
| Rizatriptan | 5 mg | 50 mg |
| Sulphuric Acid (conc.) BP | 0.91 mg | 9.1 mg |
| Bulk Water for Injections Ph. Eur. | to 1 mil | to 1 ml |

| | Example 5 | Example 6 |
|---|---|---|
| Rizatriptan | 100 mg | 160 mg |
| Sulphuric Acid (conc.) BP | 18.2 mg | 29.1 mg |
| Bulk Water for Injections Ph. Eur. | to 1 ml | to 1 ml |

The rizatriptan is dissolved in the sulphuric acid previously diluted with water. The solution is made up to volume.

The formulations are filled into vials in 100 µl aliquots, the vials are sealed and are sterilized by autoclaving to 121° C. for not less than 15 minutes. Alternatively, the solutions may be sterilized by filtration and filled aseptically into sterile vials.

The formulations are administered in unit dose volumes of 100 µl to a single nostril of patients suffering from a moderate or severe migraine attack to deliver a dose of 0.5, 5, 10 or 16 mg of rizatriptan.

We claim:

1. A method for the treatment of migraine in a patient for whom administration of rizatriptan alone does not successfully treat said migraine, which method comprises administering to the patient in need of such treatment:

an amount of 2-(R)-(1-(R)-(3,5-bis(trifluoromethyl) phenyl)ethoxy)-3-(S)-(4-fluorophenyl)-4-(3-(5-oxo-1H, 4H-1,2,4-triazolo)methyl)morpholine or a pharmaceutically acceptable salt thereof, and an amount of rizatriptan such that together they give effective relief.

2. The method of claim 1 wherein the rizatriptan is in the form of its benzoate or sulfate salt.

* * * * *